(12) United States Patent
Winker et al.

(10) Patent No.: US 8,602,271 B2
(45) Date of Patent: Dec. 10, 2013

(54) DIAPHRAGM SEAL FOR USE IN A MEDICINAL AEROSOL

(75) Inventors: Theodore A. Winker, Bloomington, MN (US); Todd D. Alband, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1340 days.

(21) Appl. No.: 10/878,783

(22) Filed: Jun. 28, 2004

(65) Prior Publication Data

US 2005/0077388 A1 Apr. 14, 2005

Related U.S. Application Data

(60) Provisional application No. 60/490,635, filed on Jul. 28, 2003.

(51) Int. Cl.
| | |
|---|---|
| *B65D 83/44* | (2006.01) |
| *B65D 83/28* | (2006.01) |
| *B65D 83/14* | (2006.01) |
| *B65D 83/00* | (2006.01) |

(52) U.S. Cl.
USPC .............. 222/402.1; 222/402.24; 222/542; 239/337

(58) Field of Classification Search
USPC .............. 239/401, 56, 398, 302, 338, 337; 222/402.1, 402.24, 402.25, 402.23, 222/394, 402.2, 542; 277/431, 434, 440; 137/246, 246.21–246.23
See application file for complete search history.

(56) References Cited

U.S. PATENT DOCUMENTS

| | | | |
|---|---|---|---|
| 2,818,202 A | 12/1957 | Abplanalp | |
| 3,581,958 A | 6/1971 | Meshberg | |
| 3,998,363 A | 12/1976 | Beres et al. | |
| 4,211,347 A | 7/1980 | Mildern | |
| 4,348,135 A | 9/1982 | St. Clair | |
| 4,407,481 A * | 10/1983 | Bolton et al. | 251/353 |
| 4,919,312 A | 4/1990 | Beard et al. | |
| 5,290,539 A | 3/1994 | Marecki | |
| 5,427,282 A * | 6/1995 | Greenleaf et al. | 222/402.1 |
| 5,474,758 A | 12/1995 | Kwon | |
| 5,579,944 A | 12/1996 | Hafner et al. | |
| 5,775,321 A * | 7/1998 | Alband | 128/200.23 |
| 5,836,299 A | 11/1998 | Kwon | |
| 5,904,274 A * | 5/1999 | Warby et al. | 222/402.2 |
| 6,129,247 A | 10/2000 | Thomas et al. | |
| 6,131,777 A * | 10/2000 | Warby | 222/402.2 |

(Continued)

FOREIGN PATENT DOCUMENTS

| | | |
|---|---|---|
| FR | 1344685 A | 11/1963 |
| GB | 872187 | 7/1961 |
| GB | 2323351 | 9/1998 |

OTHER PUBLICATIONS

ASTM Designation D395-97 entitled "Standard Test Methods for Rubber Property-Compression Set" pp. 36-40.

*Primary Examiner* — Darren W Gorman

(57) ABSTRACT

The invention comprises a device for delivering an aerosol comprising a diaphragm comprising a first layer with a compression set of 30% or more and a second layer with a compression set of 20% or less. The invention also comprises a device for delivering an aerosol comprising a diaphragm comprising a first layer comprised of an uncrosslinked thermoplastic elastomer and a second layer comprised of a crosslinked rubber.

19 Claims, 2 Drawing Sheets

(56) References Cited

U.S. PATENT DOCUMENTS

| | | |
|---|---|---|
| 6,254,104 B1 | 7/2001 | Hafner |
| 6,345,740 B1 * | 2/2002 | Riebe .................. 222/402.1 |
| 6,726,220 B2 * | 4/2004 | Grimanis et al. ............. 277/584 |
| 6,866,039 B1 * | 3/2005 | Wright et al. ............ 128/203.15 |
| 6,926,178 B1 * | 8/2005 | Anderson ................. 222/402.2 |

\* cited by examiner

DIAPHRAGM SEAL FOR USE IN A MEDICINAL AEROSOL

This application claims benefit of priority to provisional patent application 60/490,635, filed Jul. 28, 2003.

The present invention relates to devices for delivering medicinal aerosols, such as metered dose inhalers for oral or nasal inhalation. In particular, this invention relates to medicinal aerosol devices equipped with a valve having a diaphragm seal comprising a layered combination of differing seal materials.

BACKGROUND OF THE INVENTION

Medicinal aerosol inhalers are commonly used to treat a number of medical conditions. Leakage and moisture ingress are two common problems that can limit the shelf life of a medicinal aerosol. Leakage of propellant from a metered dose inhaler (MDI) during storage will lead to an increase in concentration of the other components, such as drug and excipient, of the aerosol formulation. Since an MDI contains a fixed volume of formulation, changes in the formulation concentration can lead to a change in the delivery dosage of drug and excipient. This is a particular concern for products with low total fill weights, as small absolute amounts of leakage can represent a significant percentage of the total fill weight.

Thus, all propellant based MDIs use some system of seals and/or diaphragms to minimize or prevent leakage. In a conventional MDI there are two main places that must be sealed to prevent excessive leakage of the formulation, although depending on the particular canister design the number of areas to be sealed may vary. Typically a seal is made from an elastomer which forms a vapor-tight seal between two metal or plastic parts. One place to be sealed is the contact area between the canister and the ferrule. This is done with a static seal, in that no moving parts are involved once this seal is formed. Another place to seal is to allow for isolation of the metering valve from the outside of the can, which is done using a diaphragm seal. The diaphragm seal is a dynamic (i.e., reciprocating or sliding) seal, since the valve has to move in relation to the diaphragm seal in order to perform the metering function.

Numerous materials are well known in the art for use as seals in medicinal aerosols including butyl rubber, butadiene-acrylonitrile rubbers or "Buna", neoprene or polychloroisoprene, ethylene-butene, ethylene-octene, ethylene-hexene, such as in U.S. Pat. No. 5,290,539 (Marecki) and EPDM, such as in U.S. Pat. No. 5,836,299, (Kwon). It is also recognized that these materials may be blended with one or more other polymers to achieve properties representative of the individual materials, such as in U.S. Pat. No. 5,474,758 (Kwon). Likewise, alternate configurations have been proposed to reduce leakage from medicinal aerosols, such as inclusion of an additional seal to provide a dual seal configuration for sealing the canister and the ferrule, such as in U.S. Pat. No. 5,775,321 (Alband) and U.S. Pat. No. 6,129,247 (Thomas et al.).

SUMMARY OF THE INVENTION

It has now been found that using a layered combination of differing seal materials around the valve can provide performance characteristics that are not anticipated by the performance of the seal materials used individually.

In one aspect, the present invention provides a device for delivering an aerosol comprising a valve stem, a diaphragm, and a casing member having walls defining a formulation chamber and a casing aperture, wherein the valve stem passes through the diaphragm aperture and the casing aperture and is in slidable sealing engagement with the diaphragm, and wherein the first layer of the diaphragm is in sealing engagement with the casing member, the device having contained in the formulation chamber thereof a medicinal aerosol formulation. The diaphragm comprises a first layer with a compression set equal to or greater than 30% and a second layer with a compression set equal to or less than 20%, wherein the compression set is measured according to standard test method ASTM D395-97 under the conditions of 22 hours and 70° C.

In another aspect, the present invention provides a device for delivering an aerosol comprising a valve stem, a diaphragm, and a casing member having walls defining a formulation chamber and a casing aperture, wherein the valve stem passes through the diaphragm aperture and the casing aperture and is in slidable sealing engagement with the diaphragm, and wherein the first layer of the diaphragm is in sealing engagement with the casing member, the device having contained in the formulation chamber thereof a medicinal aerosol formulation. The diaphragm comprises a first layer comprised of an uncrosslinked thermoplastic elastomer and a second layer comprised of a crosslinked rubber.

Although not wishing to be bound by theory, it is thought that the first layer provides the diaphragm with the advantages of a highly deformable layer that helps to provide a very tight seal. The second layer provides the diaphragm with the advantages of a firmer elastomer that avoids long term compression set. The surprising benefit of the present invention is that the disadvantages of each layer when used individually are overcome by the presence of the other layer, thus providing a synergistic improvement not expected from the individual performance of either layer.

BRIEF DESCRIPTION OF THE DRAWINGS

Preferred embodiments of the invention will now be described in greater detail below with reference to the attached drawings, wherein.

DETAILED DESCRIPTION OF THE INVENTION

Figures 1, 2:
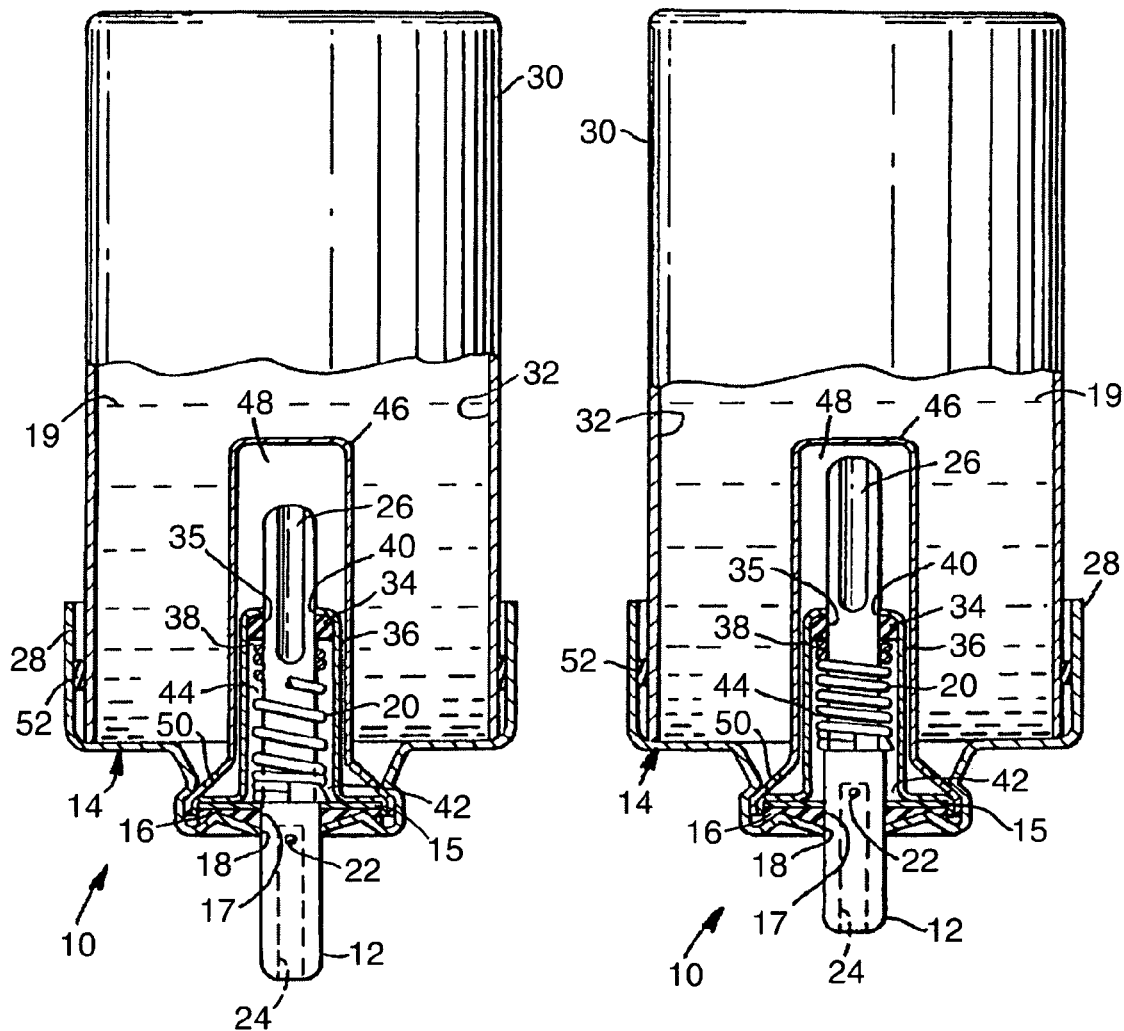
FIG. 1 is a partial cross-sectional view of one embodiment of a device of the present invention, wherein the valve stem is in the extended closed position.
FIG. 2 is a partial cross-sectional view of the embodiment illustrated in FIG. 1, wherein the valve stem is in the compressed open position.

The device of the invention will be described with reference to the drawings. FIG. 1 shows device 10 comprising valve stem 12, casing member 14, and a diaphragm comprising a first layer 16 and a second layer 15. The casing member has walls defining casing aperture 18, and the diaphragm has walls defining diaphragm aperture 17. The valve stem passes through and is in slidable sealing engagement with the diaphragm. The first layer 16 of the diaphragm is also in sealing engagement with casing member 14.

In one aspect, the first layer 16 of the diaphragm has a compression set of equal to or greater than 30% and the second layer 15 of the diaphragm has a compression set of equal to or less than 20%, wherein the compression set is measured according to standard test method ASTM D395-97 under the conditions of 22 hours and 70° C. In another aspect, the first layer 16 of the diaphragm has a compression set of equal to or greater than 40%. In another aspect, the second layer 15 of the diaphragm has a compression set of equal to or less than 15%. In still another aspect, the second layer 15 of the diaphragm has a compression set of equal to or less than 10%.

Compression set tests measure the amount of non-recoverable deformation in an elastomeric material after application of a constant force over a fixed time period at a constant temperature. This may be measured according to the American Society for Testing Materials (ASTM) standard test method D395-97. Briefly, a test sample of a fixed size is placed between two plates and compressed with a fixed force over a fixed time period (typically 22 hours) at a constant temperature (typically 70° C.). The thickness of the test sample is measured both before and after compression. The compression set is the difference between the original thickness and the final thickness of the test sample and is reported as a relative percentage of the original total thickness.

In another aspect, the first layer 16 of the diaphragm comprises an uncrosslinked thermoplastic elastomer and the second layer 15 of the diaphragm comprises a crosslinked rubber.

Materials suitable for use as the first layer of the diaphragm include polyolefin copolymers, such as ethylene copolymers with 1-butene, 1-hexene, or 1-octene of U.S. Pat. No. 5,290,539 (Marecki), the disclosure of which is herein incorporated by reference. Preferred ethylene copolymers comprise from about 80 to about 95 mole percent ethylene. Flexomer™ DFDB 1085 NT polyolefin (Union Carbide) is particularly preferred.

Materials suitable for use as the second layer of the diaphragm include neoprene or polychloroisoprene, butyl rubber, butadiene-acrylonitrile rubbers or "Buna", crosslinked ethylene-propylene (EPM) rubbers, and ethylene-propylene-diene (EPDM) rubbers.

The illustrated embodiment is a device for use with pharmaceutical formulations. The combined thickness of the diaphragm layers in the illustrated embodiment is of a thickness sufficient to form an effective seal. The combined thickness is preferably equal to or more than about 0.005 inch (127 µm), more preferably more than about 0.025 inch (635 µm), and most preferably more than about 0.040 inch (1016 µm). The combined thickness is preferably equal to or less than about 0.100 inch (2540 µm), more preferably less than about 0.075 inch (1905 µm), and most preferably less than about 0.060 inch (1524 µm). The thickness of the first and second layers may be varied independently. The relative thickness of the first layer to the thickness of the second layer is preferably equal to or less than 3:1, more preferably equal to or less than 1:1, and most preferably equal to or less than 1:2. The relative thickness of the first layer to the thickness of the second layer is preferably equal to or more than 1:50, more preferably equal to or more than 1:25, and most preferably equal to or more than 1:10. Each diaphragm layer has an outside diameter of about 0.340 inch (0.86 cm), and an inside diameter sufficient to form an effective seal with the valve stem. As mounting cups having an inside diameter of about 9.0 mm are commonly used, suitable diaphragm outside diameter can be in the range of about 8.0 mm to about 10.0 mm. As valve stems having an outside diameter of about 0.110 inch (2.79 mm) are commonly used, suitable diaphragm inside diameter can be in the range of about 0.080 inch (2.03 mm) to about 0.105 inch (2.67 mm). Furthermore, both the outside and inside diameters of the diaphragm layers may be independently selected. For example, different inside diameters may be preferred if the first and second layers of the diaphragm have different amounts of swelling when in contact with the composition of the aerosol formulation. Diaphragm dimensions suitable for use with other general types of devices can be easily selected by those skilled in the art.

Valve stem 12 is in slidable engagement with both the first layer 16 and the second layer 15 of the diaphragm. Helical spring 20 holds the valve stem in an extended closed position as illustrated in FIG. 1. Valve stem 12 has walls defining orifice 22 which communicates with exit chamber 24 in the valve stem. The valve stem also has walls defining channel 26.

In the illustrated embodiment casing member 14 comprises mounting cup 28 and canister body 30 and defines formulation chamber 32. The illustrated embodiment further comprises tank seal 34 having walls defining tank seal aperture 35, and metering tank 36 having inlet end 38, inlet aperture 40, and outlet end 42. The metering tank also has walls defining metering chamber 44 of predetermined volume (e.g., 50 µL). Outlet end 42 of metering tank 36 is in sealing engagement with the second layer 15 of the diaphragm, and valve stem 12 passes through inlet aperture 40 and is in slidable engagement with tank seal 34.

When device 10 is intended for use with a suspension aerosol formulation it further comprises retaining cup 46 fixed to mounting cup 28 and having walls defining retention chamber 48 and aperture 50. When intended for use with a solution aerosol formulation retaining cup 46 is optional. Also illustrated in device 10 is sealing member 52 in the form of an O-ring that substantially seals formulation chamber 32 defined by mounting cup 28 and canister body 30. Sealing member 52 preferably comprises the elastomeric copolymer described above.

Operation of device 10 is illustrated in FIGS. 1 and 2. In FIG. 1, the device is in the extended closed position. Aperture 50 allows open communication between retention chamber 48 and formulation chamber 32, thus allowing the aerosol formulation to enter the retention chamber. Channel 26 allows open communication between the retention chamber and metering chamber 44 thus allowing a predetermined amount of aerosol formulation to enter the metering chamber through inlet aperture 40. The first layer 16 and second layer 15 of the diaphragm seals the outlet end 42 of the metering tank.

FIG. 2 shows device 10 in the compressed open position. As valve stem 12 is depressed channel 26 is moved relative to tank seal 24 such that inlet aperture 40 and tank seal aperture 35 are substantially sealed, thus isolating a metered dose of formulation within metering chamber 44. Further depression of the valve stem causes orifice 22 to pass through aperture 18 and into the metering chamber, whereupon the metered dose is exposed to ambient pressure. Rapid vaporization of the propellant causes the metered dose to be forced through the orifice, and into and through exit chamber 24. Device 10 is commonly used in combination with an actuator that facilitates inhalation of the resulting aerosol by a patient.

Figure 3:
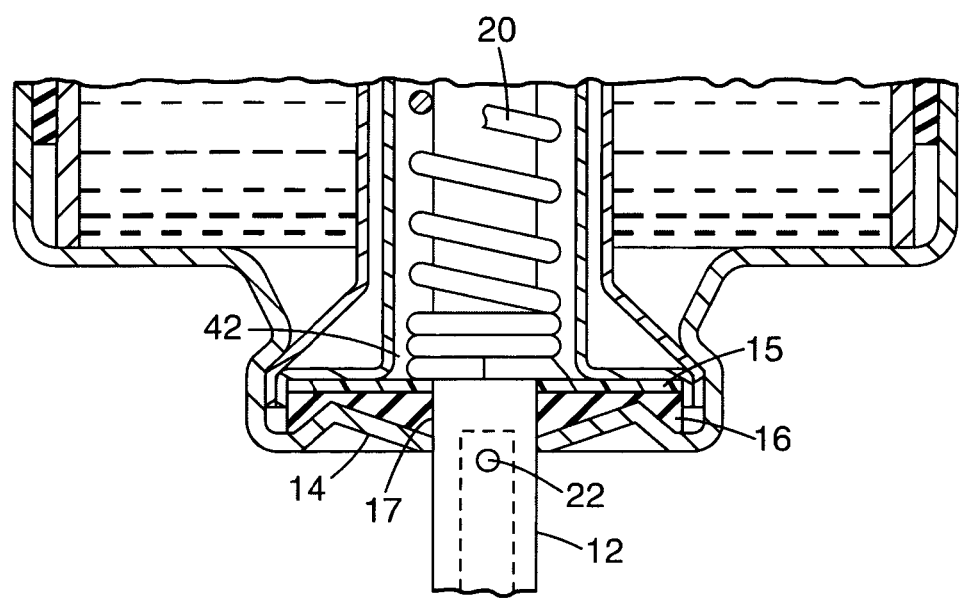
FIG. 3 is an exploded, partial cross-sectional view of the area surrounding the diaphragm aperture of one embodiment of a device of the present invention.

FIG. 3 shows an exploded view of the area surrounding the diaphragm aperture of the device of FIG. 1. In the illustrated embodiment the first layer 16 of the diaphragm is in sealing engagement with the casing member 14 and the second layer 15 of the diaphragm is in sealing engagement with the outlet end 42 of metering tank 36. In the illustrated embodiment the first layer 16 and the second layer 15 are shown as distinct layers with different outside diameters. The two layers may, however, be formed as one integral piece.

The devices of the present invention can be used in connection with aerosol formulations involving propellants such as fluorotrichloromethane, dichlorodifluoromethane, and 1,2-dichlorotetrafluoroethane. However, this invention finds particular use with aerosol formulations involving a propellant comprising 1,1,1,2-tetrafluoroethane (HFC-134a) or 1,1,1,2,3,3,3-heptafluoropropane (HFC-227). Any such formulation can be used. Pharmaceutical formulations are preferred.

Preferred pharmaceutical formulations generally comprise HFC-134a, HFC-227, or a mixture thereof in an amount effective to function as an aerosol propellant, a drug having local or systemic action and suitable for use by inhalation, and any optional formulation excipients. In a preferred embodiment, pharmaceutical formulations of the present invention comprise from 1 to 25% ethanol by weight of the total formulation.

Exemplary drugs having local effect in the lung include bronchodilators such as albuterol, formoterol, pirbuterol, and salmeterol, and pharmaceutically acceptable salts and derivatives thereof, and steroids such as beclomethasone, fluticasone, and flunisolide, and pharmaceutically acceptable salts, derivatives, solvates, and clathrates thereof. Exemplary drugs having systemic effect include peptides such as insulin, calcitonin, interferons, colony stimulating factors, and growth factors.

The drug is present in the formulation in an amount sufficient to provide a predetermined number of therapeutically effective doses by inhalation, which can be easily determined by those skilled in the art considering the particular drug in the formulation. Optional excipients include cosolvents (e.g., ethanol, water) and surfactants (e.g., oleic acid, sorbitan esters, polyoxyethylenes, glycols) and others known to those skilled in the art.

EXAMPLES

Leakage Rate Method

Aerosol devices were allowed to stand for at least 24 hours prior to testing. Aerosol devices were weighed individually, placed in a specified storage condition (e.g., room temperature or 40° C.) and reweighed after a specified time. An annual leakage rate was calculated in mg/year. Aerosol devices were identified in a way that does not contribute to the adsorption or release of moisture. Weighing was performed at room temperature. Aerosol devices to be tested were equilibrated to room temperature (RT). The results shown are an average of the value determined from 6 individual devices.

Valve Delivery Method

Aerosol devices were allowed to stand for at least 72 hours prior to testing. Testing was performed at room temperature. Aerosol devices to be tested were equilibrated to room temperature. The aerosol device was primed by placing the device in an actuator, shaking, and then actuating the device while holding it in an inverted position. This step was repeated three additional times for a total of four priming shots. A minimum five second delay was taken in between each priming shot. The primed aerosol device was removed from the actuator and weighed to the nearest 0.0001 g. The primed aerosol device was then placed in the actuator, fired while in an inverted position, removed from the actuator, and weighed to the nearest 0.0001 g. The difference in weight of the aerosol device before and after this firing was recorded as the valve delivery (in mg). The results shown are an average of the value determined from 6 individual devices.

Compression Set Method

Samples were tested according to ASTM D395 Test Method A, Compression Set Under Constant Force in Air. Test samples consisted of disks with nominal diameters of 25 mm, which were stacked to obtain a total test sample thickness of approximately 12 mm. An MTS Alliance 100 tester was used to apply a constant force of 400 lbs over a period of 22 hrs. The sample was held at a temperature of 70° C. during testing. Total sample thickness was measured before compression and after release of compression. The compression set was calculated as the difference of these two measurements reported as a relative percentage of the original thickness. Values reported below are an average of two test replicates.

Example 1

15-mL aluminum aerosol vials were each cold filled with approximately 9 g of a 90/10 (w/w) HFA-134A and ethanol mixture. All vials were fitted with 50 µL valves having 0.110 inch (2.79 mm) outer diameter, stainless steel valve stems. An approximately 10 mm outer diameter, approximately 0.1 inch (2.54 mm) inner diameter, 0.015 inch (381 µm) thick layer (shown as 16 in FIG. 3) of ethylene-butene copolymer (Union Carbide DFDB-1085) was placed between the aluminum ferrule and an approximately 8.5 mm outer diameter, 0.097 inch (2.46 mm) inner diameter, 0.038 inch (965 µm) thick layer of nitrile rubber (DB-218, American Gasket and Rubber, Chicago, Ill.) layer (shown as 15 in FIG. 3) during valve assembly. Aerosol devices were placed in a water bath at 55° C. for 3 minutes. After removal from the water bath, 5 shots were fired from each aerosol device. Leakage rates were tested at both ambient and elevated temperature (40° C.) conditions and the results are reported in Table 1. Valve delivery was 59.9 (st. dev.=0.5) mg. The compression set of the ethylene-butene copolymer was 48.2%. The compression set of the nitrile rubber was 5.5%.

Example 2

An aerosol device was prepared as in Example 1, except that the 0.015 inch (381 µm) thick layer of ethylene-butene copolymer (Union Carbide DFDB-1085) had an approximately 8.5 mm outer diameter and an approximately 0.1 inch (2.54 mm) inner diameter. Leakage rates were tested at both ambient and elevated temperature (40° C.) conditions and the results are reported in Table 1. Valve delivery was 60.7 (st. dev.=0.3) mg.

Example 3

15-mL aluminum aerosol vials were each cold filled with approximately 9 g of a 90/10 (w/w) HFA-134A and ethanol mixture. All vials were fitted with 50 µL valves having 0.110 inch (2.79 mm) outer diameter, stainless steel valve stems. An approximately 8.5 mm outer diameter, 0.09 inch (2.29 mm) inner diameter, 0.050 inch (1.27 mm) thick layer (shown as 16 in FIG. 3) of ethylene-butene copolymer (Union Carbide DFDB-1085) was placed between the aluminum ferrule and an approximately 8 mm outer diameter, 0.1 inch inner diameter, 0.017 inch (432 µm) thick layer of nitrile rubber (DB-218, American Gasket and Rubber, Chicago, Ill.) layer (shown as 15 in FIG. 3) during valve assembly. Aerosol devices were placed in a water bath at 55° C. for 3 minutes. After removal from the water bath, 5 shots were fired from each aerosol device. Leakage rates were tested at both ambient and elevated temperature (40° C.) conditions and the results are reported in Table 1. Valve delivery was 59.5 (st. dev.=0.5) mg.

Comparative Example 1

An aerosol device was prepared as in Example 1, except that the 0.015 inch (381 μm) thick layer of ethylene-butene copolymer (Union Carbide DFDB-1085) was not included. Leakage rates were tested at both ambient and elevated temperature (40° C.) conditions and the results are reported in Table 1.

Comparative Example 2

An aerosol device was prepared as in Example 1, except that the nitrile rubber layer was placed between the aluminum ferrule and ethylene-butene copolymer layer. That is, the order of the diaphragm layers was reversed. Leakage rates were tested at both ambient and elevated temperature (40° C.) conditions and the results are reported in Table 1.

Comparative Example 3

An aerosol device was prepared as in Example 3, except that the nitrile rubber layer was placed between the aluminum ferrule and ethylene-butene copolymer layer. That is, the order of the diaphragm layers was reversed. Leakage rates were tested at both ambient and elevated temperature (40° C.) conditions and the results are reported in Table 1.

TABLE 1

| | Leakage Rate [mg/year] | | | | | |
|---|---|---|---|---|---|---|
| Storage condition | Ex. 1 | Ex. 2 | Ex. 3 | Comp. Ex. 1 | Comp. Ex. 2 | Comp. Ex. 3 |
| Ambient, 1 week | 58 | 57 | 76 | 186 | 79 | 107 |
| 40° C., 1 week | 47 | 49 | 105 | 374 | 211 | 202 |
| 40° C., 2 week | 67 | 69 | 117 | 384 | 236 | 218 |

We claim:

1. A device for delivering an aerosol comprising:
   a valve stem;
   a diaphragm having walls defining a diaphragm aperture, the diaphragm comprising a first layer in contact with the valve stem with a compression set equal to or greater than 30% and a second layer in contact with the valve stem with a compression set equal to or less than 20%, wherein the compression set is measured according to standard test method ASTM D395-97 under the conditions of 22 hours and 70° C.; and
   a casing member having walls defining a formulation chamber and a casing aperture, wherein the valve stem passes through the diaphragm aperture and the casing aperture and is in slidable sealing engagement with the diaphragm, and wherein the first layer of the diaphragm having the compression set equal to or greater than 30% is in sealing engagement with the casing member, the device having contained in the formulation chamber thereof a medicinal aerosol formulation.

2. A device according to claim 1, wherein the first layer comprises a copolymer comprising ethylene.

3. A device according to claim 2, wherein the copolymer comprises about 80 to about 95 mole percent ethylene.

4. A device according to claim 3, wherein the copolymer comprises 1-butene.

5. A device according to claim 1, wherein the second layer comprises a rubber selected from the group consisting of nitrile, butyl, and EPDM.

6. A device according to claim 1, wherein the relative thickness of the first layer to the second layer is equal to or less than 1:2.

7. A device according to claim 1, wherein the medicinal aerosol formulation comprises
   1,1,1,2-tetrafluoro ethane, 1,1,1,2,3,3,3-heptafluoropropane, or a mixture thereof, in an amount effective to function as a propellant.

8. A device according to claim 7, wherein the medicinal aerosol formulation comprises about 1 to about 25% by weight ethanol.

9. A device according to claim 1, wherein the second layer comprises a crosslinked thermoplastic elastomer.

10. A device according to claim 1, wherein the amount of medicinal aerosol formulation in the formulation chamber is less than about 900 mg.

11. A device for delivering an aerosol comprising:
    a valve stem;
    a diaphragm having walls defining a diaphragm aperture, the diaphragm comprising a first layer in contact with the valve stem comprised of an uncrosslinked thermoplastic elastomer and a second layer in contact with the valve stem comprised of a crosslinked rubber, wherein the first layer has a compression set equal to or more than 30%, the compression set being measured according to ASTM D395-97 under the conditions of 22 hours and 70° C.; and
    a casing member having walls defining a formulation chamber and a casing aperture, wherein the valve stem passes through the diaphragm aperture and the casing aperture and is in slidable sealing engagement with the diaphragm, and wherein the first layer of the diaphragm having a compression set equal to or greater than 30% is in sealing engagement with the casing member, the device having contained in the formulation chamber thereof a medicinal aerosol formulation.

12. A device according to claim 11, wherein the first layer comprises a copolymer comprising ethylene.

13. A device according to claim 12, wherein the copolymer comprises about 80 to about 95 mole percent ethylene.

14. A device according to claim 13, wherein the copolymer comprises 1-butene.

15. A device according to claim 11, wherein the second layer comprises a rubber selected from the group consisting of nitrile, butyl, and EPDM.

16. A device according to claim 11, wherein the relative thickness of the first layer to the second layer is equal to or less than 1:2.

17. A device according to claim 11, wherein the medicinal aerosol formulation comprises 1,1,1,2-tetrafluoroethane, 1,1,1,2,3,3,3-heptafluoropropane, or a mixture thereof, in an amount effective to function as a propellant.

18. A device according to claim 17, wherein the medicinal aerosol formulation comprises about 1 to about 25% by weight ethanol.

19. A device according to claim 11, wherein the amount of medicinal aerosol formulation in the formulation chamber is less than about 900 mg.

* * * * *

UNITED STATES PATENT AND TRADEMARK OFFICE
CERTIFICATE OF CORRECTION

PATENT NO. : 8,602,271 B2  
APPLICATION NO. : 10/878783  
DATED : December 10, 2013  
INVENTOR(S) : Ted Winker Page 1 of 1

It is certified that error appears in the above-identified patent and that said Letters Patent is hereby corrected as shown below:

In the Specification

Column 4
Line 45, Delete "seal 24" and insert -- seal 34 --, therefor.

In the Claims

Column 8
Line 9, In Claim 7, delete "tetrafluoro ethane," and insert -- tetrafluoroethane, --, therefor.

Signed and Sealed this
Twenty-third Day of December, 2014

Michelle K. Lee
*Deputy Director of the United States Patent and Trademark Office*